United States Patent
Nilson

[19]

[11] Patent Number: 5,906,201
[45] Date of Patent: May 25, 1999

[54] HEAT AND MOISTURE EXCHANGER

[75] Inventor: Billy Nilson, Mjölby, Sweden

[73] Assignee: Louis Gibeck AB, Uplands Vasby, Sweden

[21] Appl. No.: 08/849,055

[22] PCT Filed: Nov. 30, 1995

[86] PCT No.: PCT/SE95/01444

§ 371 Date: May 29, 1997

§ 102(e) Date: May 29, 1997

[87] PCT Pub. No.: WO96/16689

PCT Pub. Date: Jun. 6, 1996

[30] Foreign Application Priority Data

Dec. 1, 1994 [SE] Sweden .................................. 9404182

[51] Int. Cl.[6] .............................................. A61M 15/00
[52] U.S. Cl. ............................ 128/203.16; 128/203.17; 128/203.26; 128/203.27; 128/204.17
[58] Field of Search ................... 128/203.17, 203.26, 128/203.27, 204.17, 201.13, 203.16

[56] References Cited

U.S. PATENT DOCUMENTS

| | | | |
|---|---|---|---|
| 3,288,556 | 11/1966 | Weber, III | 128/203.27 |
| 3,820,540 | 6/1974 | Hirtz et al. | 128/203.27 |
| 4,291,838 | 9/1981 | Williams | 128/203.27 |
| 4,327,717 | 5/1982 | Oetjen, et al. | 128/201.13 |
| 4,750,484 | 6/1988 | Le Pabic | 128/203.27 |
| 4,825,863 | 5/1989 | Dittmar et al. | 128/204.17 |
| 5,063,921 | 11/1991 | Howe | 128/203.27 |
| 5,109,471 | 4/1992 | Volker Lang | 392/396 |
| 5,435,298 | 7/1995 | Anthony | 128/203.27 |
| 5,460,172 | 10/1995 | Eckerbom et al. | 128/205.12 |
| 5,577,494 | 11/1996 | Kuypers et al. | 128/205.12 |
| 5,590,644 | 1/1997 | Rosenkoetter | 128/205.12 |
| 5,647,344 | 7/1997 | Turnbull | 128/205.12 |
| 5,769,071 | 6/1998 | Turnbull | 128/203.17 |

*Primary Examiner*—Aaron J. Lewis
*Attorney, Agent, or Firm*—Banner & Witcoff, Ltd.

[57] ABSTRACT

A moisture-heat exchange arrangement which is intended for connection to a patient to humidify and heat the air inhaled by the patient, wherein the arrangement includes a moisture-heat exchanger unit (5) and a humidifier means (11, 12) that connects with the unit (5) to increase the humidity of the inhalation air. The humidifying means includes a casing (3) which is connected with the moisture-heat exchanger unit (5) and which has a first opening (9) that communicates with the moisture-heat exchanger unit and an opposing opening (6) that communicates with the patient. The inner surface of the casing has provided thereon a water-absorbing and/or water-vapour permeable material (11) which delivers moisture to the air inhaled by the patient.

10 Claims, 2 Drawing Sheets

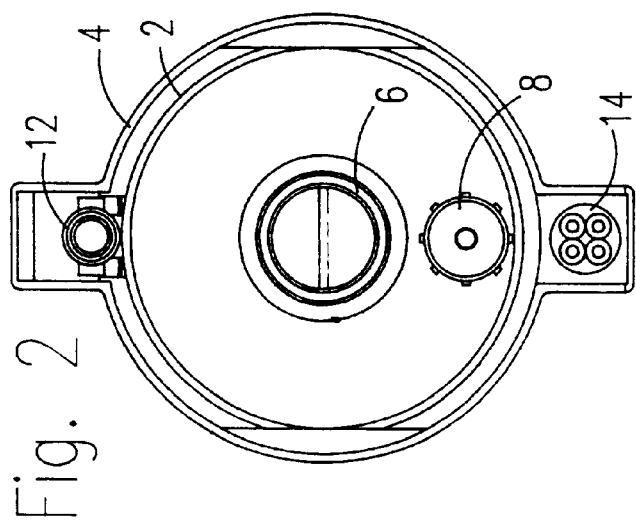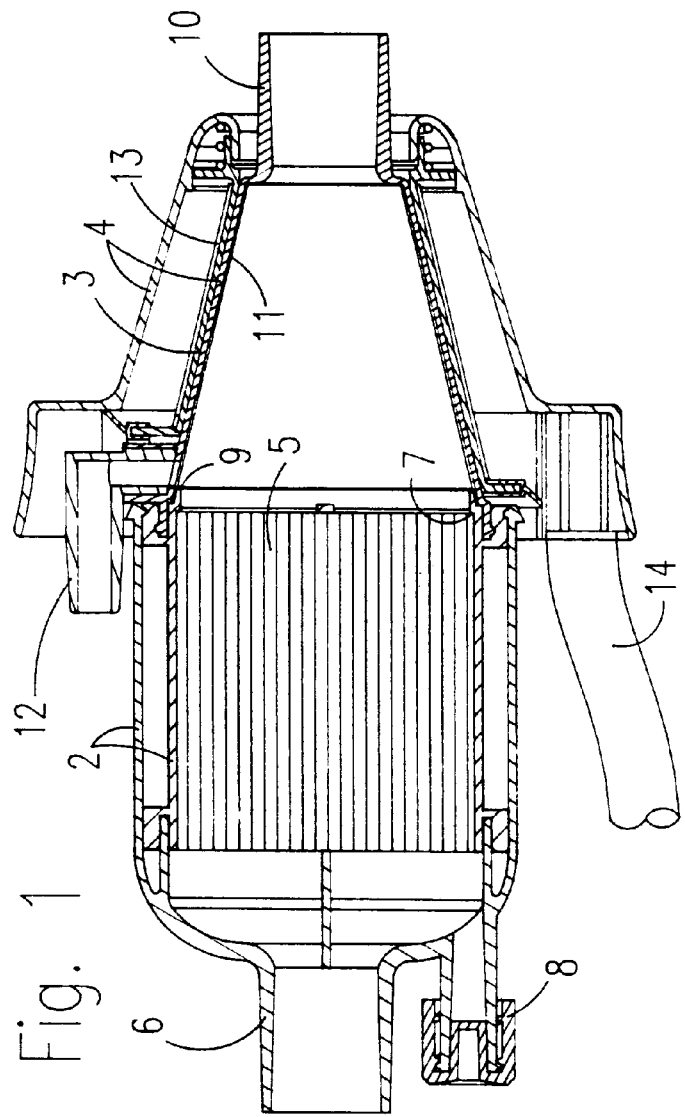

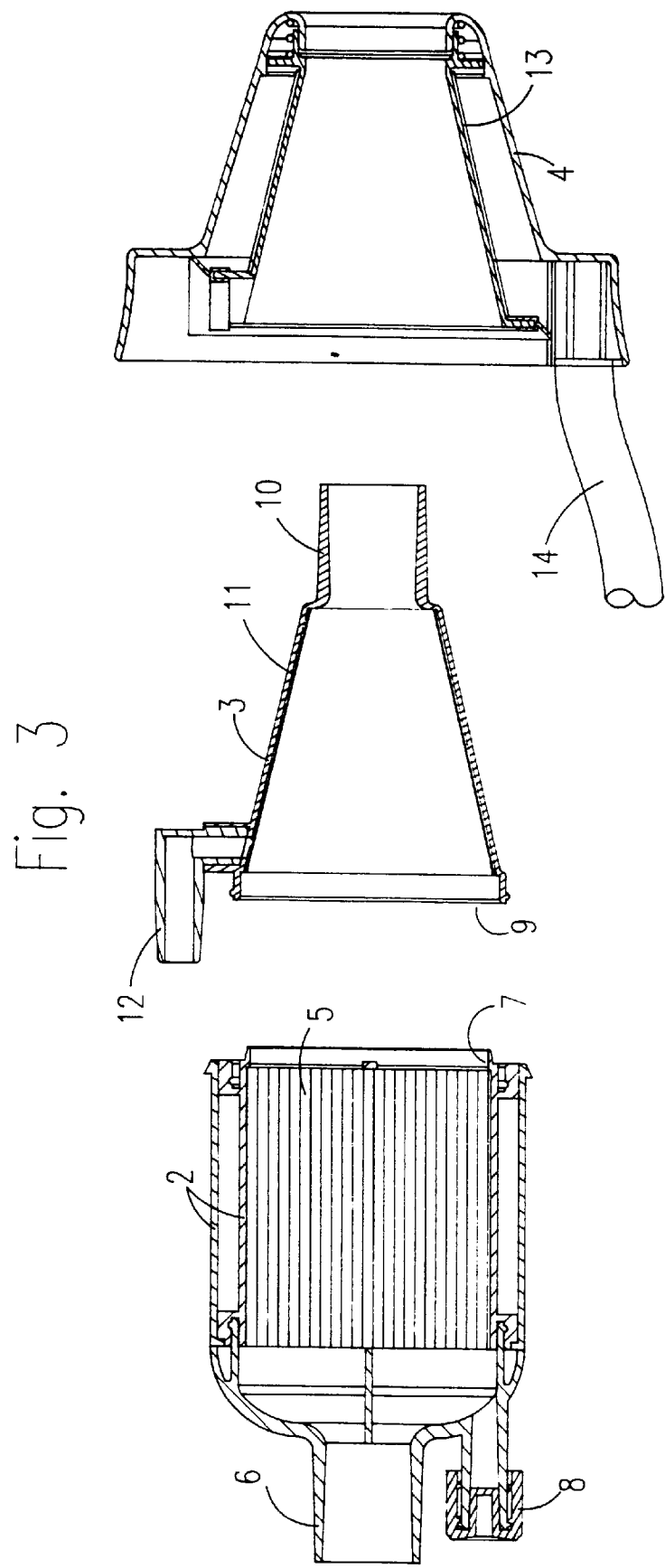

HEAT AND MOISTURE EXCHANGER

TECHNICAL FIELD

The present invention pertains to heat-moisture exchange arrangements for connection to a patient with the intention of humidifying and heating the patient's inhalation air. The heat and moisture exchanger is normally connected to a respirator on the side thereof distal from the patient.

DESCRIPTION OF THE BACKGROUND ART

Moisture-heat exchangers of the aforesaid kind are known to the art. One such moisture-heat exchanger is disclosed in U.S. Pat. No. 5,109,471. This known moisture-heat exchanger is comprised of two passive moisture-heat exchanger elements and an intermediate air humidifying and heating arrangement. Moistening of the inhalation air is achieved with water that is introduced into water passageways such as to wet a perforated paperboard plate which covers the end surface on the inside of one moisture-heat exchanger element. The water is heated in the moisture-heat exchanger with the aid of resistors that function to heat heat-transfer means which include a perforated plate and which are mounted between the two passive moisture-heat exchanger elements.

The air humidifying means of the known apparatus presents considerable resistance to the flow of air through the moisture-heat exchanger and therewith reduces the rate of air flow and also the throughflow of inhalation and exhalation air. This resistance to air flow is mainly caused by the fact that the perforated plates cover large parts of the through-flow area.

Because of the construction of the heating means of the known SUBSTITUTE SHEET (RULE 26) apparatus, the air that flows through the heating means is heated only partially and, furthermore, unevenly. Because the heating means is located in a region between two passive moisture-heat exchange elements, the moisture-heat exchanger has a large axial extension.

DE-A 4 126 028 teaches a moisture-heat exchanger apparatus which includes a moisture-heat exchanger element that accommodates a plurality of pipes through which water is delivered to said element and therewith moisten the same. This known apparatus also includes a heating means which comprises an annular heating element which is spaced from the moisture-heat exchanger element both radially and axially. The greatest drawback with this apparatus is that water is delivered to only a few discrete regions within the moisture-heat exchanger element, resulting in uneven moistening of the inhalation air.

WO91/19527 teaches a moisture-heat exchanger apparatus which includes a moisture-heat exchanger element in the form of a plate, and an inhalation-air heating resistor spaced from the plate. The apparatus also includes a pipe whose outlet orifice is located adjacent the surface of the resistor and which delivers water thereto. The greatest drawbacks with this apparatus are mainly that moistening of the air is ineffective because water is delivered to the resistor, which also creates the risk of short-circuiting, and because heating of the air is incomplete when the resistor has the form of a rod, or the through-passage of air is impaired when the resistor has the form of a grid or grating.

SE-C 501 042 teaches a moisture-heat exchanger in which a band-like or wire-like heating element is mounted between layers therein that are positioned parallel with the direction of flow of the inhalation air. Manufacture of this apparatus is complicated and the apparatus presents a relatively high resistance to air flow. An air humidifying means in the form of a diffusion rod lies against one end of the moisture-heat exchanger and delivers moisture thereto. However, delivery of moisture to the moisture-heat exchanger is uneven and often incomplete, therewith rendering the apparatus less effective.

SUMMARY OF THE INVENTION

An object of the present invention is to eliminate at least partially the drawbacks of earlier known moisture-heat exchangers and to provide a moisture-heat exchange arrangement by means of which inhalation air will be moistened and heated (warmed) uniformly and effectively, and by means of which inhalation air will be heated without the heating means coming into contact with moist air, and which will present a low resistance to the flow of inhalation air.

This object is fulfilled with an inventive arrangement having the characteristic features set forth in the characterizing clauses of the following claims.

BRIEF DESCRIPTION OF THE DRAWINGS

FIG. 1 is a longitudinal section view of an inventive arrangement;

FIG. 2 is an end view of the arrangement as seen from the left in FIG. 1; and

FIG. 3 is a longitudinal section view corresponding to the view of FIG. 1 but with the arrangement components being shown separated from one another.

DETAILED DESCRIPTION OF PREFERRED EMBODIMENTS

The arrangement illustrated in FIGS. 1–3 includes first, second and third casings 2, 3 and 4, all of which have a circular cross-sectional shape and all of which are made of rigid plastic material, preferably transparent material. The first casing 2, which is circular-cylindrical, is preferably joined permanently to the second casing 3 after having inserted a circular-cylindrical heat-exchanger unit 5 into the casing 2 and after having inserted into the casing 3 a conical element 11 made of water absorbing material.

The casing 2 is a double-wall insulating casing and is provided with an inlet pipe 6 for connection to, e.g., a respirator (not shown), and an outlet opening 7. A tubular outlet connector 8 which receives a Luer fitting for gas-measuring purposes is provided adjacent the inlet connector 6 and communicates with the interior of the casing 2 through a hole provided in said casing.

The outer cylindrical surface of the moisture-heat exchanger unit 5 abuts with or is slightly spaced from the inner wall of the casing 2. Unit 5 is comprised of a hygroscopic material that has good moisture and heat-exchanging properties and is in the form of a band which is wound helically such as to form a plurality of generally concentrical layers which extend generally parallel with the flow direction of the inhalation air. The unit may, for instance, be of the kind which is included in a moisture-heat exchanger marketed by Gibeck Respiration AB under the trademark Humid-Vent 2S and which includes a band which is wound helically to a cylindrical form and which is comprised of a smooth-surface paper layer and a corrugated paper layer attached thereto, said layers being optionally treated with a bactericidal or germicidal substance or some other substance.

The second casing 3 is conical and includes an inlet opening 9 and an outlet connecting pipe 10 which is intended for connection to a patient. A conically shaped element 11 abuts the inner surface of the casing 3, between the opening 9 and the outlet connecting pipe 10. The conical element 11 will preferably cover the whole of the inner surface of the casing, although preferably not in contact with the unit 5. The conical element 11 has the form of a sheet of material which will take-up or absorb water. Alternatively, the element 11 may have the form of a semi-permeable membrane, for instance a polypropylene membrane, which is permeable to moisture/water vapour. Because of the large surface area of the element 11 and because of its conical shape, it is ensured that a major part of the patient's inhalation air will come into contact with the absorbent material. Because no part of the material 11 is located in the flow path of the inhalation air and because the inhalation air will only sweep across the material, the flow resistance is low.

The casing 3 is provided with an inlet pipe 12 which transports water into the casing at a position adjacent the opening 9. The water is spread between the inner surface of the casing 3 and the material 11 and into said material so as to wet the same.

The third casing 4 is a double-wall casing whose inner wall is suitably made of metal and has the same conicity as the outer surface of the casing 3. The axial extension of the casing 4 is such that the outlet pipe metal 10 will project from the casing 4 when said casing is detachably fitted onto the casing 3. A heating element 13 is disposed between the two walls of the casing 4. The element 13 may be comprised of a ring-wound strip of electrically conductive plastic material having a Positive Temperature Coefficient (PTC) or a metal coil that has a resistive effect, for instance aluminium foil. The element 13 is enclosed sealingly in the casing 4 and connected to a conductor 14 which, in turn, is connected to a source of electric current (not shown).

The inventive arrangement is intended for connection in a system intended to improve the breathing conditions of a patient. Thus, the inlet pipe connector 6 is connected to a respirator (not shown) and the outlet pipe connector 10 is connected to the patient. During the inhalation phase of the patient, inhalation air flows from the respirator through the pipe connector 6 and out through the outlet pipe connector 10 to the patient, via the casing 2, 3 and 4, wherewith the unit 5 heats and moistens the air. Heating and moistening of the air is achieved as a result of the unit 5 being heated and moistened by the exhalation air in the preceding exhalation phase, and also because the heating element 13 propagates heat to said conically shaped material 11 and the water contained therein, via the inner wall of the casing 4 and the wall of the casing 3. The material 11 and its water content are heated to a temperature which will ensure that sufficient vapour will pass through the material and into the casing 3. This vapour mixes with the inhalation air and heats and moisturizes the air generally uniformly.

The exhalation air flows in the opposite direction through the arrangement as the patient breathes out, therewith cooling that part of the unit 5 which lies closest to the inlet pipe 6 and de-moisturize the air prior to delivering the air to a respirator, for instance.

Although the present invention has been described and illustrated with reference to an exemplifying embodiment thereof, it will be understood that other embodiments and modifications thereto are conceivable within the concept of the invention. The invention is therefore limited solely by the contents of the following claims.

I claim:

1. A moisture-heat exchange arrangement for connection to a patient for humidifying and heating the air inhaled by a patient, wherein the arrangement includes a moisture-heat exchanger unit and humidifying means that connect with the unit for increasing the humidity of the inhalation air, said humidifying means includes a casing which is connected with the moisture-heat exchanger unit, said casing includes an inner surface, a first opening that communicates with the moisture-heat exchanger unit and an opposing opening that communicates with a patient, said inner surface of the casing has provided thereon a water-absorbing and/or water-vapour permeable material which delivers moisture to the air inhaled by the patient, and a fluid passageway formed by said inner surface extending between said first opening and said opposing opening, and said humidfying means also includes a heating means positioned completely outside said fluid passageway.

2. An arrangement according to claim 1, characterized in that the material covers a substantial part of the inner surface of the casing and has a tubular configuration.

3. An arrangement according to claim 2, characterized in that the material covers the whole of the inner surface of said casing.

4. An arrangement according to claim 1 or claim 2, characterized in that the casing is conical and the first opening is larger than the opposing opening.

5. An arrangement according to claim 4, characterized in that the material has a conical configuration and is concentrical with the casing.

6. An arrangement according to claim 1 or claim 2, characterized in that the material is a semi-permeable membrane, preferably comprised of polypropylene or like material.

7. An arrangement according to claim 1 or claim 2, characterized by said heating means being detachably disposed on an outside surface of the casing.

8. An arrangement according to claim 7, characterized in that the heating means includes a double-wall casing with a heating element disposed between said walls.

9. An arrangement according to claim 8, characterized in that the inner wall of the double-wall casing is tubular and surrounds the casing connected to the moisture-heat exchanger unit.

10. An arrangement according to claim 9, characterized in that the inner wall of the double-wall casing is conical and has the same conicity as and lies in abutment with the outer surface of the casing connected to the moisture-heat exchanger unit.

* * * * *